United States Patent [19]
Akiba et al.

[11] Patent Number: 5,888,191
[45] Date of Patent: Mar. 30, 1999

[54] CONDUIT-SEPARATED ENDOSCOPE SYSTEM

[75] Inventors: Haruo Akiba; Seiki Yamaguchi, both of Omiya, Japan

[73] Assignee: Fuji Photo Optical Co., Ltd., Omiya, Japan

[21] Appl. No.: 14,045

[22] Filed: Jan. 27, 1998

[30] Foreign Application Priority Data

Feb. 14, 1997 [JP] Japan .................................... 9-047339

[51] Int. Cl.$^6$ ........................................................ A61B 1/12
[52] U.S. Cl. ............................ 600/153; 600/156; 600/159
[58] Field of Search .................................... 600/121, 123, 600/153, 154, 155, 156, 157, 158, 159

[56] References Cited

U.S. PATENT DOCUMENTS 5,447,148 9/1995 Oneda et al. ....................... 600/159 X

*Primary Examiner*—Beverly M. Flanagan
*Attorney, Agent, or Firm*—Ronald R. Snider

[57] ABSTRACT

An endoscope system of the present invention makes it possible to pass a cleaning brush through all conduits, simplify cleaning, and perform disinfection such as sterilization by an autoclave. The system is an endoscope for controlling the opening/closing of various conduits by an solenoid valve unit, in which a conduit unit is removably set to the joint at the rear end of an operating portion and a conduit to be connected to various conduits at the main frame side is set to the conduit unit. Moreover, a second cable which is used separately from a first cable in which an electric-signal transmission line is set is provided for the conduit unit to lead said conduit to the solenoid-valve unit. Thereby, it is possible to separately clean the conduit unit by removing it from the main frame. Therefore, cleaning is simplified and the conduit unit can be sterilized by an autoclave or the like.

5 Claims, 5 Drawing Sheets ated endoscope system, particularly to the structure of an endoscope system provided with conduits such as a suction tube and an air-feed/water-feed tube and making it possible to easily clean the conduits.

CONDUIT-SEPARATED ENDOSCOPE SYSTEM

BACKGROUND OF THE INVENTION

This application claims the priority of Japanese Patent Application No. 9-47339 filed on Feb. 14, 1997, which is incorporated herein by reference.

1. Field of the Invention

The present invention relates to a conduit-separated endoscope system, particularly to the structure of an endoscope system provided with conduits such as a suction tube and an air-feed/water-feed tube and making it possible to easily clean the conduits.

2. Description of the Prior Art

FIG. 7 shows the entire structure of the electronic endoscope (scope) of a conventional electronic endoscope system. The electronic endoscope 1 comprises a front end 1A having a CCD (Charge Coupled Device), an inserting portion 1B, an operating portion 1C, and a cable 1D. An end of the cable 1D is provided with a connector 2A for connecting a light guide and various conduits and a connector 2B for connecting an electric signal transmission line. The operating portion 1C is provided with angle dial 3 for bending the front end 1A, a suction button (mechanical control valve) 4A, and an air-feed/water-feed button 4B and moreover, a forceps port 5 for inserting an action tool into the front end side.

An action-tool inserting channel communicated with the forceps port 5, a suction tube for suction, and an air feed tube and a water feed tube for feed air or water are arranged in the endoscope, and a conduit connector 7 for connecting these conduits with external tubes is set to the connector 2A.

According to the above structure, the connector 2A is connected to a light source unit, the connector 2B is connected to a processor unit, and the inside of an object to be observed is picked up and observed by the CCD of the front end 1A in accordance with light irradiation by the light guide. Moreover, air or water can be fed to an observation window or the like from the front end 1A by using the air-feed or water-feed tube and insertion of the action tool and suction of dirt in the object to be observed can be performed by using the suction tube.

BRIEF SUMMARY OF THE INVENTION

Object of the Invention

However, because the endoscope system is used in a medical treatment site, it is necessary to clean and sterilize the above various conduits. However, there is a problem that the cleaning and sterilization cannot be efficiently performed. That is, though the above conduits are cleaned by using a brush, it is impossible to pass the brush from the front end 1A up to the conduit connector 7 (2A) at a time. This is because the entire endoscope is very long, there is a sharply bent portion particularly in the operating portion 1C among an internal conduit, and it is difficult to advance the brush to the inside as far as possible because a conduit is complicated (or cut at a portion) when using valves for controlling opening and closing operations with a mechanical structure as the suction button 4A and air-feed/water-feed button 4B.

Conventionally, it is necessary to flow cleaning water for a long time and improve the control valve so that the cleaning brush reaches the inside as far as possible. Therefore, the cleaning operation is troublesome and the structure of each portion for cleaning is complicated.

Moreover, in the case of an electronic endoscope, it is impossible to perform the sterilization using an autoclave like other medical equipment because a CCD serving as an image pickup device and circuits for driving and controlling the CCD are arranged and various members are bonded to the endoscope by an adhesive. Therefore, a lot of time is required for the sterilization using a germicidal solution.

SUMMARY OF THE INVENTION

The present invention is made to solve the above problems and its object is to provide a conduit-separated endoscope system making it possible to pass a cleaning brush through all conduits, simply cleaning, and perform sterilization such as disinfection with an autoclave.

To achieve the above object, the present invention comprises an endoscope in which a transmission line for electric signals is set and various conduits are arranged, an operating portion which is set to the rear end of the endoscope and in which a joint opening the conduits is provided for an end, a first cable which is connected to the operating portion and in which the electric-signal transmission line is set, a solenoid valve unit for opening or closing the conduits in the endoscope, a conduit separably connected to the joint of the operating portion, a conduit unit in which a second cable formed separately from the first cable to lead the conduit up to the solenoid valve unit is set, and connection means for removably connecting the conduit unit with the joint of the operating portion. In this case, the first and second cables can use any structure and they are used as flexible connection lines.

According to the above structure, the conduit unit is removable from the operating portion by the connection means and therefore, the unit can be handled separately from the main frame. Thus, it is possible to clean the main frame side separately from the conduit unit by a cleaning brush and moreover, sterilize the conduit unit with an autoclave because there is no electrical structure.

In the operating portion, it is possible to almost linearly arrange the conduit up to the rear end along the extension line of the axis line of the endoscope inserting portion and connect the conduit unit to the rear end. Thereby, insertion of a cleaning brush into the main frame from the rear end of the operating portion and cleaning of the brush are simplified.

The connection means can use a structure in which the aperture of a conduit and a catching portion on whose outer periphery a male screw is formed are arranged on the operating portion and a rotary body on which a female screw to be screwed to the catching portion is rotatably set to the outer periphery of the joint of the conduit unit side.

Moreover, another aspect of the present invention is characterized by including an endoscope in which an electric-signal transmission line is set and various conduits are arranged, a first cable which is connected to the endoscope and in which at least the electric-signal transmission line is set, and a second cable which is set to the endoscope separately from the first cable and in which only a conduit is set.

DETAILED DESCRIPTION OF THE PREFERRED EMBODIMENTS

Figure 1:
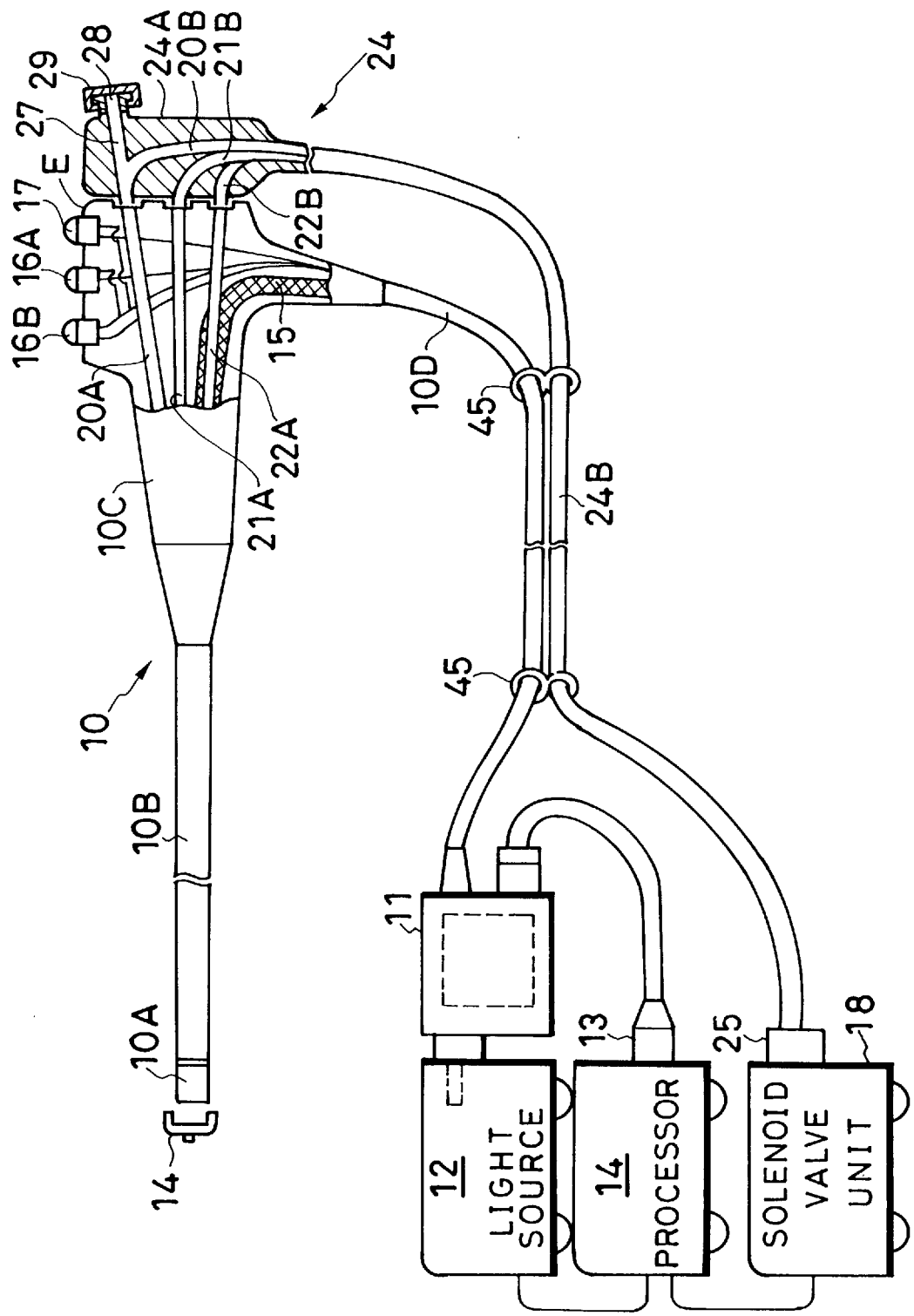
FIG. 1 is a local sectional view showing the structure of the conduit-separated endoscope system of an embodiment of the present invention.

FIG. 1 shows the structure of the conduit-separated endoscope system of an embodiment. The endoscope system controls a conduit by a solenoid valve. In FIG. 1, an electronic endoscope 10 comprises a front end 10A having a CCD serving as an image pickup device, an inserting portion 10B, an operating portion 10C, and a first cable 10D. The connector 11 of the first cable 10D is connected to a light source unit 12 and a connector 13 provided for a signal cable branched from the connector 11 is connected to a processor (image processing) unit 14.

That is, the endoscope 10 is provided with a light guide for applying light from the front end 10A and a signal line 15 for drive-controlling the CCD and reading an image signal. The light guide is extended to the light source unit 12 from the front end 10A through the first cable 10D and the signal line 15 is extended to the processor unit 13 from the front end 10A through the first cable 10D.

Moreover, the operating portion 10C is provided with a not-illustrated angle dial and moreover, a suction button 16A serving as an electrical switch, a air-feed/water-feed button (two-stage switch) 16B, and a hard-copy button 17. Furthermore, the portion 10C is provided with a solenoid value unit 18 electrically connected to the processor unit 14. Though details are described later, the solenoid valve unit 18 performs suction and air-feed/water-feed operations by receiving a control signal and controlling opening/closing of an internal solenoid valve in accordance with the operations of the suction button 16A and the air-feed/water-feed button 16B.

Furthermore, a suction tube 20A, air-feed tube 21A, and water-feed tube 22A are arranged in the main frame of the endoscope 10. As illustrated, these tubes 20A, 21A, and 22A concerned are linearly formed toward a rear end E at the operating portion 10C along the extension line of the axis line of the inserting portion 10B. Thereby, an advantage is obtained that a cleaning brush can be easily inserted from the rear end E of the operating portion 10C.

Furthermore, a conduit unit 24 is set so as to be removable from the rear end E of the operating portion 10C. That is, the conduit unit 24 comprises a support portion 24A, a second cable 24B, and a connector 25 to be connected to the solenoid valve unit 18, and a suction tube 20B, air-feed tube 21B, and water-feed tube 22B to be connected to the conduits 20A, 21A, and 22A at the main frame side are arranged on the support portion 24A, and these tubes 20B, 21B, and 22B are extended up to the solenoid valve unit 18 by passing through the second cable 24B.

Figure 7:
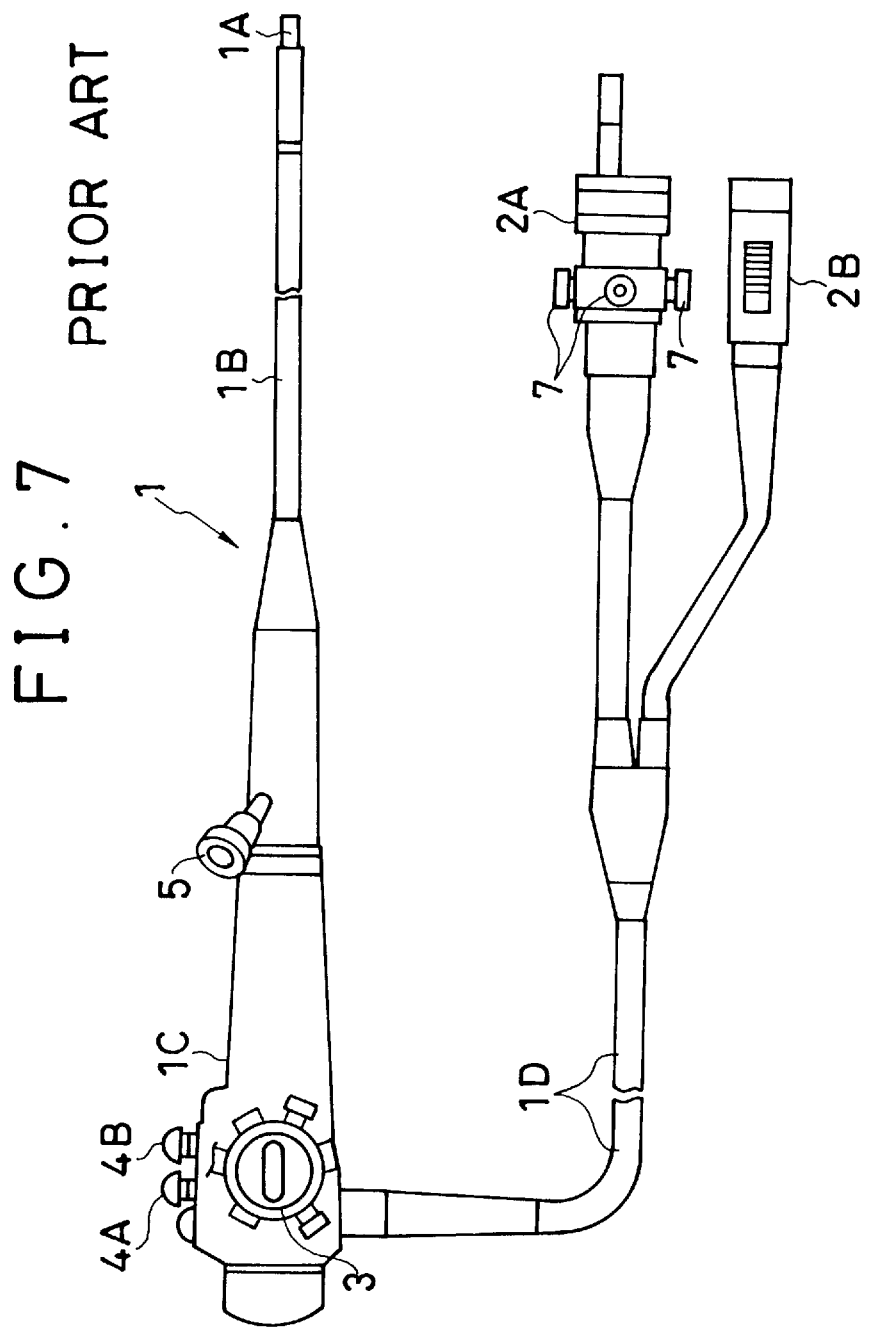
FIG. 7 is an illustration showing the entire structure of a conventional endoscope.

Furthermore, a forceps port 28 is provided for the suction tube 20B through a branch tube 27. As shown in FIG. 7, the forceps port 5 conventionally set to the front of the operating portion 1C is moved and set to the conduit unit 24 in the case of this example. Moreover, a rubber cap 29 is set to the forceps port 28.

Figure 2:
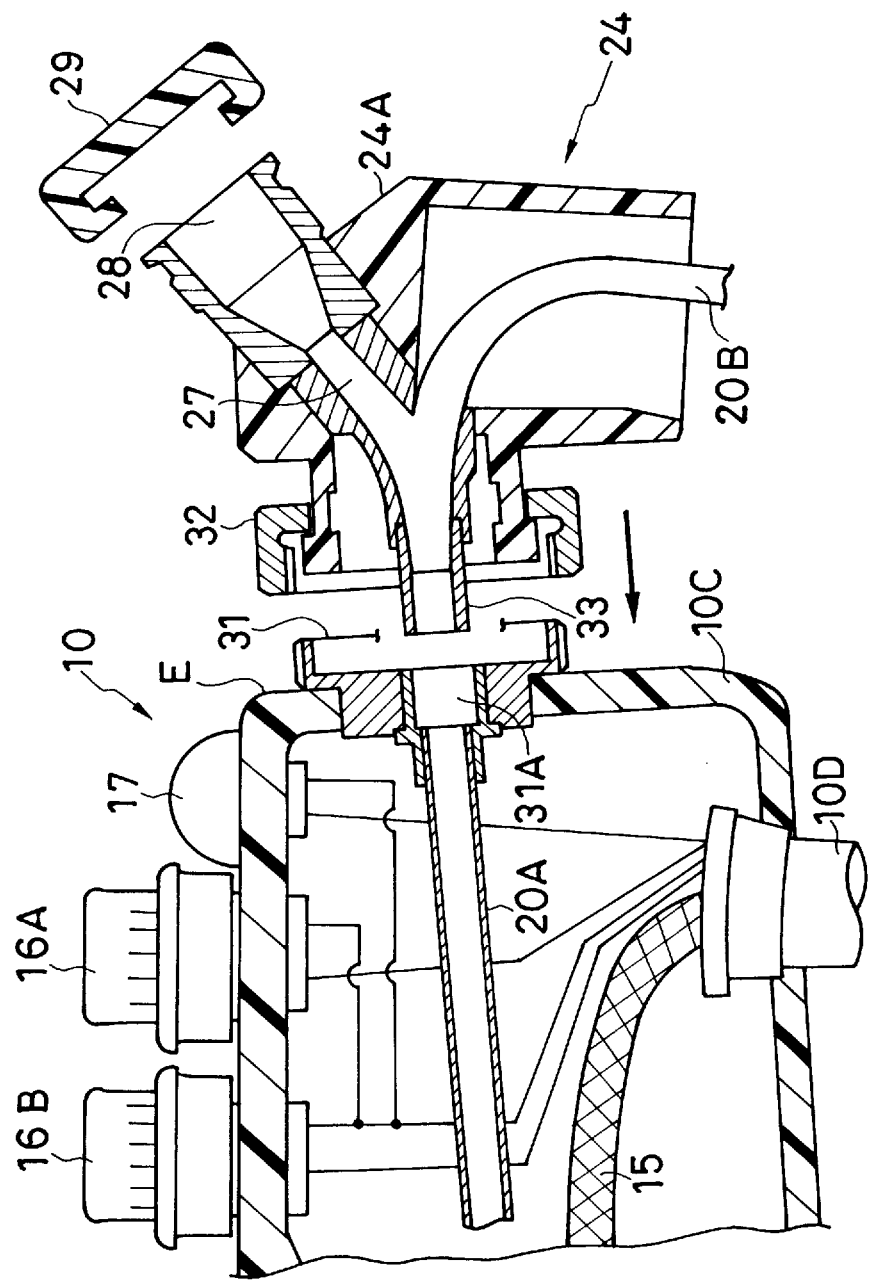
FIG. 2 is a sectional view showing an example of the joint between the operating portion and the conduit unit of an embodiment.

FIG. 2 shows an example of the connection structure between the operating portion 10C and the conduit unit 24 and this example uses screw-fixing connection means (connector). That is, a catching portion 31 on whose outer periphery a male screw is formed is set to the rear end E of the operating portion 10C, and a rotary body 32 on whose inner periphery a female screw is formed is provided for the support portion 24A of the conduit unit 24. The rotary body 32 is set so that it can rotate and slide forward and backward for the cylindrical portion of the support portion 24A. Moreover, the suction tube 20A is connected to a connection hole 31A in the catching portion 31 and a protruded tube 33 is set to the suction tube 20B at the other conduit unit 24 side. Furthermore, other air-feed tubes 21A and 21B and water-feed tubes 22A and 22B are constituted similarly to the case of the suction tubes 20A and 20B through not illustrated.

According to the above structure, the suction tubes 20A and 20B are connected to each other by screwing the rotary body 32 to the catching portion 31 while inserting the protruded tube 33 of the suction tube 20B into the connection hole 31A and fixing them with screws. Though FIG. 2 shows a state in which the cap 29 is removed from the forceps port 28, the cap 29 is set so that the forceps port 29 is brought into an airtight state when performing suction without using the forceps port 29.

Figure 3:
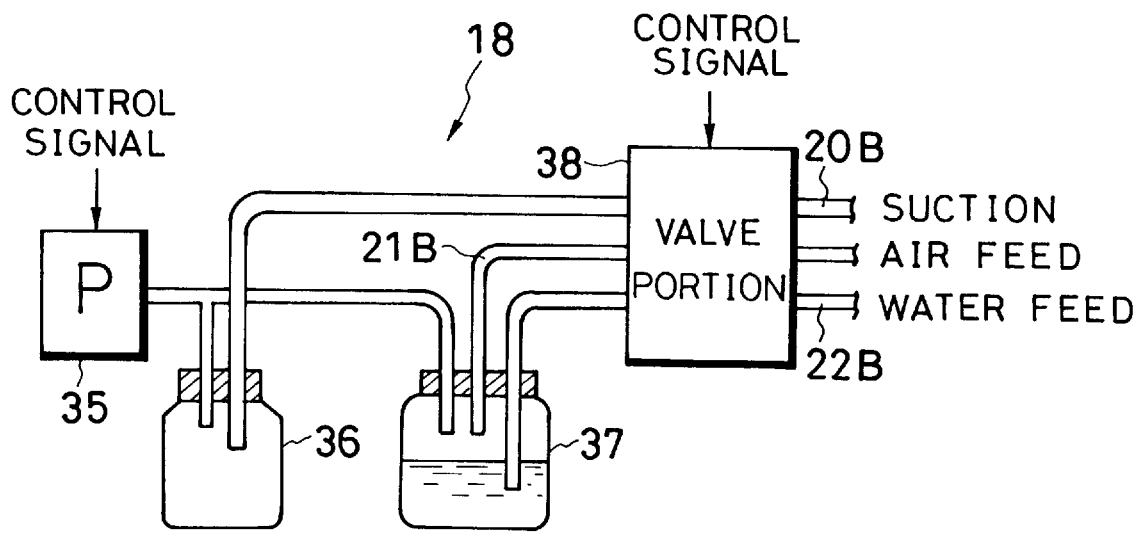
FIG. 3 is an illustration showing an example of the structure of the solenoid valve unit of an embodiment.

FIG. 3 shows a schematic structure of the inside of the solenoid valve unit 18. As illustrated, the solenoid valve unit 18 is provided with a valve portion 38 for controlling the opening/closing of each conduit by using a pump 35 (which may be divided into 2, a suction pump and an air-feed/water-feed pump) a suction tank 36, an air-feed/water-feed tank 37, and a solenoid valve.

In the case of the solenoid valve unit 18, the solenoid valve of the valve portion 38 is driven in accordance with on/off control signals supplied from the suction button 16A and air-feed/water-feed button 16B of the operating portion 10C. For example, when the suction button 16A is pressed, suction is executed by a pump 35 and simultaneously, only the suction tube 20B is opened by the valve portion 38 and suction is performed through the suction tube 20B. Moreover, by slightly pressing the air-feed/water-feed button 16A by only one stage, air is fed by the pump 35 and simultaneously, only the air-feed tube 21B is opened and air can be fed. By pressing the air-feed/water-feed button 16B up to two stages, only the water-feed tube 21B is opened under an air-feed state and water in the tank 37 can be fed.

Figure 4:
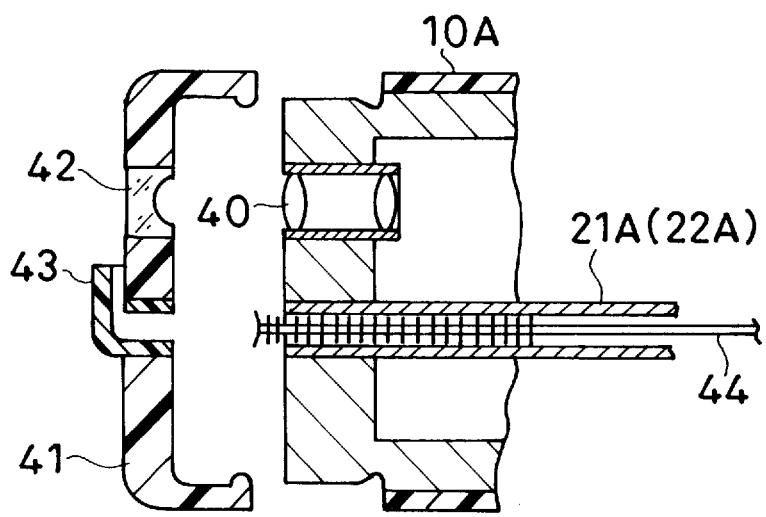
FIG. 4 is a sectional view showing the structure of the front end in FIG. 1.

FIG. 4 shows the structure of the front end 10A of an embodiment. At the front end 10A of this embodiment, a front-end cap can be removed for cleaning. That is, an objective optical system 40 or the like is set to the front end 10A and the air-feed tube 21A and water-feed tube 22A are united into one tube. For example, a front-end cap 41 is set so as to be fitted to the outer periphery of the front end 10A. An observation window 42 is provided for the front-end cap 41 and an injection nozzle 43 for feeding air or water is provided for the observation window 42. The structure of the front end 10A has advantages that the injection nozzle 43 does not interrupt a cleaning brush 44 when inserting the brush 44 from the operating portion 10C side and moreover, the brush 44 can be inserted from the front end 10A as shown in FIG. 4.

Figure 5:
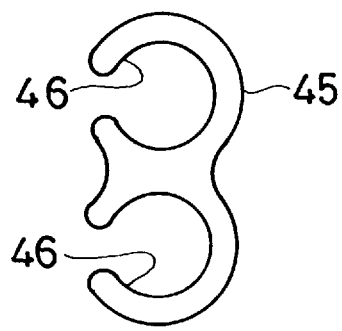
FIG. 5 is an illustration showing a fastener for putting the first and second cables of an embodiment.

FIG. 5 shows a fastener for putting the first cable 10D and second cable 24B together. As shown in FIG. 5, the fastener 45 comprises an elastic body made of plastic or the like. A fitting portion 46 having a circular hole is formed at two places of the fastener 45 and the first cable 10D and second cable 24B are put together by fitting the cables into the fitting portions 46 one each.

This embodiment has the above structure and the conduit 24 can be handled by removing it from the main frame of the endoscope having the operating portion 10C and first cable 10D. Therefore, these components can be separately cleaned and sterilized and the cleaning brush (44) can be made to pass through all the tubes 20A, 20B, 21A, 21B, 22A, and 22B. Moreover, because the front-end cap 41 can be removed, it is 25 possible to completely apply the cleaning brush 44 to the front end 10A.

Moreover, in the case of this embodiment, because each conduit at the operating portion 10C is formed almost straight along the axis line of the endoscope inserting portion 10B, it is possible to easily insert the cleaning brush 44 from the rear end E of the operating portion 10C.

Furthermore, because the solenoid valve unit 18 to be set outside is used instead of the conventional mechanical-structural on-off valves (4A and 4B) arranged at an operating portion, cleaning of an on-off valve having a mechanical structure is unnecessary and a conduit is simplified. Therefore, an advantage can be obtained that cleaning is simplified.

Furthermore, because the conduit unit 24 does not have any electrical structure, advantages are obtained that disinfection can be performed by an autoclave and sterilization is simplified.

Figure 6:
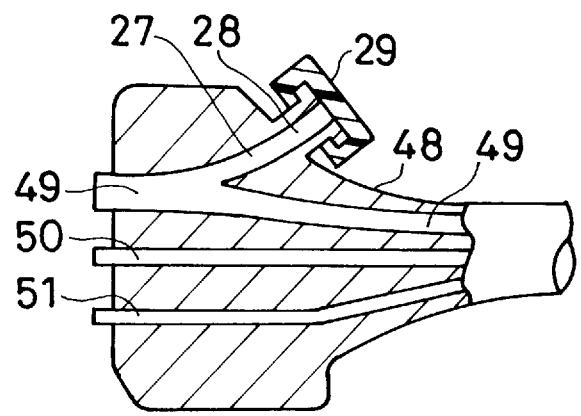
FIG. 6 is a sectional view showing another example of the structure of the conduit unit of an embodiment.

FIG. 6 shows another structure of the support portion of the conduit unit 24. In the case of the illustrated support portion 48, a suction tube 49, air-feed tube 50, and water-feed tube 51 are almost linearly arranged. This structure further simplifies the insertion of a cleaning brush.

Moreover, in the case of the above embodiment, a case is described in which three types of conduits are arranged. However, the present invention can be also applied to a case in which any one or two of a suction tube, air-feed tube, and water-feed tube is or are used. Furthermore, though a case is shown in which connection means is fixed by tightening it with a screw. However, it is possible to use other means such as mere connection of elastic bodies as the connection means.

As described above, the present invention makes it possible to handle the main frame separately from a conduit unit, pass a cleaning brush through all conduits, and simplify cleaning. Moreover, advantages are obtained that a conduit unit can be disinfected by an autoclave and sterilization is simplified.

What is claimed is:

1. A conduit-separated endoscope system comprising:
   an endoscope in which an electric-signal transmission line is set and various conduits are arranged;
   an operating portion which is set to a rear end of said endoscope and in which a joint opening said conduits is set to an end;
   a first cable which is connected to said operating portion and in which said electric-signal transmission line is set;
   a solenoid valve unit for controlling the opening/closing of the conduits in said endoscope;
   a conduit unit which is provided with a first conduit separably connected to the second conduit at the joint of said operating portion and in which a second cable formed separately from said first cable is set in order to lead the first conduit up to said solenoid valve units;
   connection means for removably connecting said conduit unit with the joint of said operating portion; and
   wherein said conduits are almost linearly extended up to a rear end of the operating portion along the extension line of the axis line of an endoscope inserting portion in said operating portion so as to connect said conduit unit to the rear end.

2. The conduit-separated endoscope system according to claim 1,
   wherein said conduit unit having a forceps port is provided for the suction tube through a branch tube.

3. A conduit-separated endoscope system comprising:
   an endoscope in which an electric-signal transmission line is set and various conduits are arranged;
   an operating portion which is set to a rear end of said endoscope and in which a joint opening said conduits is set to an end;
   a first cable which is connected to said operating portion and in which said electric-signal transmission line is set;
   a solenoid valve unit for controlling the opening/closing of the conduits in said endoscope;
   a conduit unit which is provided with a first conduit separably connected to the second conduit at the joint of said operating portion and in which a second cable formed separately from said first cable is set in order to lead the first conduit up to said solenoid valve units;
   connection means for removably connecting said conduit unit with the joint of said operating portion; and
   wherein the aperture of a conduit and a catching portion on whose outer periphery a male screw is formed are set to said operating-side joint as said connection means; and
   a rotary body with a female screw screwed to said catching portion formed on the outer periphery of its joint is rotatably set to said conduit unit side.

4. A conduit-separated endoscope system in accordance with claim 3 comprising:
   an endoscope in which an electric-signal transmission line is set and various conduits are arranged;
   an operating portion which is set to a rear end of said endoscope and in which a joint opening said conduits is set to an end;
   a first cable which is connected to said operating portion and in which said electric-signal transmission line is set;
   a solenoid valve unit for controlling the opening/closing of the conduits in said endoscope;
   a conduit unit which is provided with a first conduit separably connected to the second conduit at the joint of said operating portion and in which a second cable formed separately from said first cable is set in order to lead the first conduit up to said solenoid valve units;
   connection means for removably connecting said conduit unit with the joint of said operating portion; and
   wherein said conduits are almost linearly extended up to a rear end of the operating portion along the extension line of the axis line of an endoscope inserting portion in said operating portion so as to connect said conduit unit to the rear end;
   in which at least said electric-signal transmission line is set in said first cable; and
   the second cable which is set to said endoscope separately from said first cable and only a conduit is set in the second cable.

5. A conduit-separated endoscope system comprising:

an endoscope in which an electric-signal transmission line is set and various conduits are arranged;

an operating portion which is set to a rear end of said endoscope and in which a joint opening said conduits is set to an end;

a first cable which is connected to said operating portion and in which said electric-signal transmission line is set;

a solenoid valve unit for controlling the opening/closing of the conduits in said endoscope;

a conduit unit which is provided with a first conduit separably connected to the second conduit at the joint of said operating portion and in which a second cable formed separately from said first cable is set in order to lead the first conduit up to said solenoid valve units;

connection means for removably connecting said conduit unit with the joint of said operating portion; and wherein said conduits are almost linearly extended up to a rear end of the operating portion along the extension line of the axis line of an endoscope inserting portion in said operating portion so as to connect said conduit unit to the rear end;

in which at least said electric-signal transmission line is set in said first cable; and the second cable which is set to said endoscope separately from said first cable and only a conduit is set in the second cable.

* * * * *